(12) United States Patent
Folkesson (10) Patent No.: US 9,615,619 B2
(45) Date of Patent: Apr. 11, 2017

(54) INDICATOR DEVICES AND ARTICLES COMPRISING THE INDICATOR DEVICE

(75) Inventor: Jan L. Folkesson, Varnamo (SE)

(73) Assignee: 3M Innovative Properties Company, St. Paul, MN (US)

( * ) Notice: Subject to any disclaimer, the term of this patent is extended or adjusted under 35 U.S.C. 154(b) by 232 days.

(21) Appl. No.: 13/027,571

(22) Filed: Feb. 15, 2011

(65) Prior Publication Data

US 2011/0133103 A1 Jun. 9, 2011

Related U.S. Application Data

(63) Continuation of application No. 11/258,579, filed on Oct. 25, 2005, now abandoned, which is a continuation-in-part of application No. PCT/SE2004/001181, filed on Aug. 11, 2004.

(30) Foreign Application Priority Data

Aug. 13, 2003 (SE) ...................................... 0302216

(51) Int. Cl.
| | |
|---|---|
| *A42B 3/06* | (2006.01) |
| *G01J 1/50* | (2006.01) |
| *G01N 17/00* | (2006.01) |
| *G01N 17/04* | (2006.01) |
| *G01N 33/44* | (2006.01) |

(52) U.S. Cl.
CPC ................ *A42B 3/067* (2013.01); *G01J 1/50* (2013.01); *G01N 17/004* (2013.01); *G01N 17/043* (2013.01); *G01N 33/44* (2013.01)

(58) Field of Classification Search
CPC ........... A42B 3/067; G01J 1/50; G01N 33/44; G01N 17/043; G01N 17/004

USPC ............ 250/474.1; 422/55–60; 436/58, 902; 116/206, 278, 334, 335

See application file for complete search history.

(56) References Cited

U.S. PATENT DOCUMENTS

| | | | | |
|---|---|---|---|---|
| 3,787,687 | A |   | 1/1974 | Trumble |
| 4,185,328 | A | * | 1/1980 | Graveno ............................ 2/8.1 |
| 4,293,757 | A | * | 10/1981 | Niemi ............................ 219/147 |
| 4,478,792 | A |   | 10/1984 | McConnaughey et al. |
| 5,747,225 | A |   | 5/1998 | Manico et al. |
| 5,997,927 | A |   | 12/1999 | Gies |
| 6,054,256 | A |   | 4/2000 | Nohr et al. |
| 6,151,711 | A | * | 11/2000 | Edwards ............................ 2/8.3 |
| 2001/0019110 | A1 |   | 9/2001 | Faran et al. |

(Continued)

FOREIGN PATENT DOCUMENTS

| | | |
|---|---|---|
| EP | 1123814 A2 | 3/1996 |
| JP | 10-036690 | 2/1998 |

(Continued)

OTHER PUBLICATIONS

"Welding Health Hazards", U.S. Department of Labor OSHA Office of Training and Education May 1996.*

*Primary Examiner* — Shogo Sasaki (57) ABSTRACT

An indicator device comprising a first carrier material; a first pigment disposed in the first carrier material, the first pigment capable of being degraded by exposure to UV radiation; and wherein the first carrier material is configured so as to have a varying thickness such that upon exposure to UV radiation, a visible change in the pigment will occur which will result in a varying visible change over a first surface of the first carrier material.

17 Claims, 4 Drawing Sheets

(56) References Cited

U.S. PATENT DOCUMENTS

| | | | |
|---|---|---|---|
| 2001/0039671 A1* | 11/2001 | Robinson et al. | 2/7 |
| 2002/0084423 A1 | 7/2002 | Ferralli | |
| 2003/0110548 A1* | 6/2003 | Robinson et al. | 2/8 |
| 2006/0063883 A1 | 3/2006 | Folkesson | |

FOREIGN PATENT DOCUMENTS

| | | |
|---|---|---|
| JP | 10-36690 | 2/1998 |
| JP | 2002-257810 | 9/2002 |
| KR | 1019960000121 | 6/1999 |
| WO | WO 95/01896 | 1/1995 |
| WO | WO 00/35726 | 6/2000 |
| WO | WO 2005/016045 | 2/2005 |

* cited by examiner

INDICATOR DEVICES AND ARTICLES COMPRISING THE INDICATOR DEVICE

CROSS REFERENCE TO RELATED APPLICATION

This application is a continuation of U.S. Ser. No. 11/258,579, filed Aug. 11, 2004, which claims priority from International Application No. PCT/SE2004/001181, filed Aug. 11, 2004, which claims priority from Swedish Application No. SE302216-7 filed Aug. 13, 2003, the disclosures of which is incorporated by reference in its entirety herein.

BACKGROUND

The present disclosure relates to indicator devices for determining the ageing of articles (e.g., plastic articles), which are degradable by ultraviolet (UV) radiation.

Plastic is a material that can be used in many contexts. For example, plastic is employed in the manufacture of different consumer related products. More particularly, since plastic withstands impact and is readily/cost effectively formed into different shapes, plastic is suited for use in safety and personal protection articles (e.g., helmets (e.g., construction helmets, bike helmets, ski helmets, and the like), car and bicycle seats for children, and the like).

One drawback of plastic is that it degrades under the action of UV radiation. For example, the presence of UV radiation leads to cracks in plastics of all different types. Further, it is noted that degradation of the plastic article in the absence of UV radiation can be minimal (e.g., when the plastic article is packed and stored in boxes/containers). Differences in the speed of ageing are also observed depending on whether the plastic article is used indoors or outdoors and whether the plastic article is used in northerly or southerly latitudes. In other words, the UV radiation exposure of the plastic article can be a decisive factor in the speed of aging of the plastic article.

Figure 1:
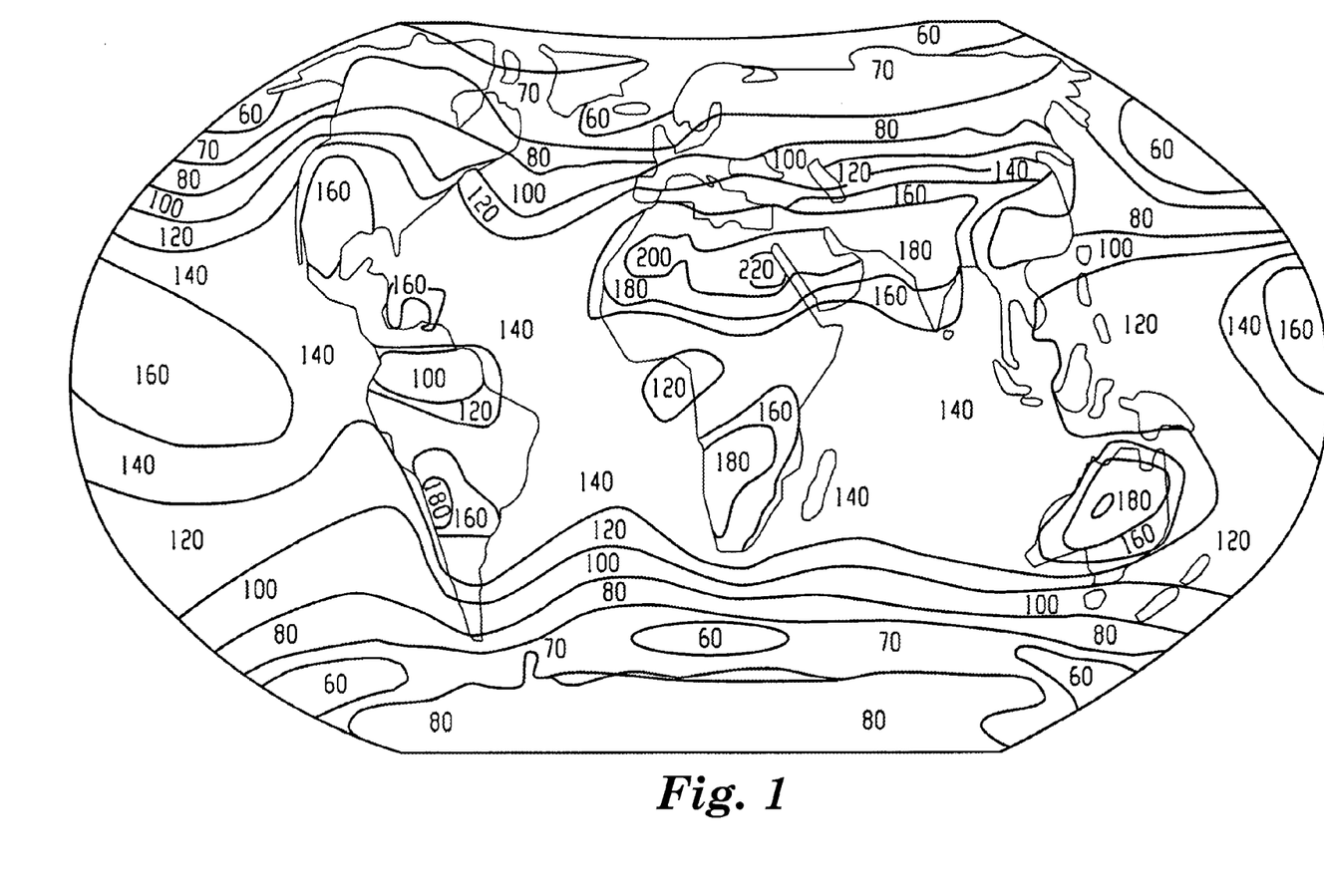
FIG. 1 is a graphical representation of generalized isolines of global radiation.

Referring to FIG. 1, a graphical representation of generalized isolines of global radiation is illustrated. The global UV radiation per year is measured according to ASTM D1435. The intensity of UV radiation illustrated in FIG. 1 is measured in kLy (kilo-Langley), which represents how much UV radiation energy falls on a centimeter square area $(cm^2)$ per year. FIG. 1 illustrates that the intensity of UV radiation varies depending on geographical location. For example, the intensity of UV radiation is more intense in the deserts of Africa compared to a city in Western Europe. As such, the useful lifetime of a plastic article varies depending on the geographical location of its use, since some areas receive a greater intensity of UV radiation than other areas.

Presently, a "date marking" is disposed on a plastic article to provide a consumer with an estimated lifetime of the article. When a date marking is employed, considerable safety margins are employed in order to be certain that an aged article whose mechanical strength is defective is no longer used. For example, the date marking is set based on an assumed time limit for the product to reach maximum UV exposure. As such, this date marking might not adequately reflect the useful life of the article (e.g., in the above example, a plastic article ages faster than the date marking in some areas, particularly in the deserts of Africa). Further, date marking can, in many cases, lead to usable articles, which have not been exposed to UV radiation and have not aged, becoming unsellable when their date marking has expired. However, in order to avoid injury to a person or damage to property, the date marking is honored. By erring on the side of caution by respecting the date marking, considerable economic losses are suffered by manufactures, retailers, end-users, and the like, who might have stored large quantities of the dated marked articles.

Further, a time period for use of an article can be set by mandate, for example, by a legislative restriction set by a given country, which can differ from country to country. Again, the actual durability (lifetime) of a plastic article can exceed a given time period set by a legislature. As such, removing an article from use prematurely (i.e., before its useful life has expired) can further cause economic losses to be suffered, since the article would be replaced more frequently compared to replacing the article when its useful lifetime has expired.

Accordingly, what is needed in the art are indicator devices that can measure the ageing of articles that degrade with UV radiation exposure.

SUMMARY

Disclosed herein are indicator devices and articles comprising the indicator device.

One embodiment of an indicator device comprises a first carrier material; a first pigment disposed in the first carrier material, the first pigment capable of being degraded by exposure to UV radiation; and wherein the first carrier material is configured so as to have a varying thickness such that upon exposure to UV radiation, a visible change in the pigment will occur which will result in a varying visible change over a first surface of the first carrier material.

Another embodiment of an indicator device comprises a first carrier material; a first pigment disposed in the first carrier material, the first pigment capable of being degraded by exposure to UV radiation; a second carrier material disposed in contact with the first carrier material; and a second pigment disposed in the second carrier material, the second pigment capable of being degraded by exposure to UV radiation, wherein the second pigment has a different fastness to light than the first pigment such that a visible change in indicator device occurs from the first carrier material to the second carrier material.

A third embodiment of an indicator device comprises a carrier material; a first pigment disposed in the carrier material, the first pigment capable of being degraded by exposure to UV radiation; and a marking concealed by the first pigment, the marking capable of being visible upon degradation of the first pigment.

One embodiment of an article comprises a surface; an indicator device disposed in physical communication with the surface, the indicator device comprising a first carrier material; a first pigment disposed in the first carrier material, the first pigment capable of being degraded by exposure to UV radiation; and wherein the first carrier material is configured so as to have a varying thickness such that upon exposure to UV radiation, a visible change in the pigment will occur which will result in a varying visible change over a first surface of the first carrier material.

The above-described and other features will be appreciated and understood by those skilled in the art from the following detailed description, drawings, and appended claims.

BRIEF DESCRIPTION OF DRAWINGS

Referring now to the figures, which are exemplary embodiments, and wherein the like elements are numbered alike.

DETAILED DESCRIPTION

Disclosed herein are indicator devices for determining the ageing of articles that are degradable by UV radiation exposure. More particularly, as will be explained in greater detail throughout this disclosure, it has been discovered that a formulation comprising a pigment capable of degrading when exposed to UV radiation can be employed in an UV indicator device to measure the UV exposure of an article to provide a visible indication of the useful life of the article to the end user of the article. Reference is made to articles comprising plastic (hereinafter referred to as plastic articles) for ease in discussion, with the understanding that any article comprising a material that degrades when exposed to UV radiation is within the scope of this disclosure.

The terms "first," "second," and the like herein do not denote any order or importance, but rather are used to distinguish one element from another, and the terms "a" and "an" herein do not denote a limitation of quantity, but rather denote the presence of at least one of the referenced items. The modifier "about" used in connection with a quantity is inclusive of the stated value and has the meaning dictated by the context (e.g., includes the degree of error associated with measurement of the particular quantity). Unless defined otherwise herein, all percentages herein mean weight percent ("wt. %"). Furthermore, all ranges disclosed herein are inclusive and combinable (e.g., ranges of "up to about 25 weight percent (wt. %), with about 5 wt. % to about 20 wt. % desired, and about 10 wt. % to about 15 wt. % more desired," are inclusive of the endpoints and all intermediate values of the ranges, e.g., "about 5 wt. % to about 25 wt. %, about 5 wt. % to about 15 wt. %", etc.).

The indicator device comprises a formulation comprising a carrier material and a pigment capable of degrading when exposed to UV radiation. The carrier material is any material that acts as a matrix for the pigment. For example, suitable carrier materials include plastics, textiles, ceramics, and the like. For ease in discussion, reference is made hereinafter to a carrier material comprising plastic, with the understanding that the disclosure can readily be adapted for use with other materials. When the carrier material comprises plastic, the indicator device further comprises a UV stabilizer. Without wanting to be bound by theory, by UV stabilizing the plastic, the fading function of the pigment of the plastic is primarily (e.g., greater than 50%) related to visual light (e.g., light having a wavelength of about 400 nanometers (nm) to about 800 nm). Various optional additives can be added to the formulation depending on the desired application.

Further, the carrier material comprises a material that has a useful life greater than or equal to the useful life of the article that is to be measured when exposed to UV radiation. The carrier material is selected such that it is compatible with the pigment. While embodiments are envisioned where the carrier material of the indicator device comprises the same material as the plastic article, the indicator device can comprise materials other than those employed in the plastic article. In one embodiment, the carrier material comprises a plastic (e.g., polycarbonate, polyethylene, polypropylene, and the like, and combinations comprising at least one of the foregoing). For example, the carrier material can comprise polyethylene, which is economical, environmentally friendly, capable of being molded (e.g., injection molded), easily UV stabilized, and easily colored with the pigment.

The carrier material is present in a sufficient amount to act as a matrix for the pigment. For example, the carrier material is present in an amount of greater than or equal to about 90 wt. %, particularly greater than or equal to about 95 wt. %, wherein weight percents are based on a total weight of the formulation. In other embodiments, the carrier material is present in an amount of about 95 wt. % to about 99 wt. %.

The properties of the pigment and the material thickness of the indicator device are selected such that the color degradation of the indicator device occurs at a rate sufficient to track the useful life of the plastic article. Stated another way, degradation of the pigment under the action of UV radiation corresponds to the degradation (e.g., crack formation) of the plastic article. Without wanting to be bound by theory, factors to consider in designing the indicator device to correspond to the degradation of the plastic article include, but are not limited to, the choice of pigment, the concentration of the pigment in the formulation, the fastness to light, and the material thickness of the indicator.

In other embodiments, the indicator device is designed such that the pigment and the thickness are selected in such a manner that the degradation of the pigment corresponds to a maximum permitted UV exposure of the article for a given market or regulations. For example, an indicator device can be obtained which indicates when an active use (i.e., exposure to UV radiation) during a predetermined period of time has been achieved. Stated another way, the indicator device indicates the life of an article based on UV radiation exposure. As such, when an article is not being exposed to UV radiation, the degradation of the pigment is mitigated or eliminated (e.g., when the article is stored indoors) corresponding to a reduction or discontinuation in the ageing of the article.

The fastness to light of the pigment indicates the speed of degradation under the action of light, in particular UV light. Fastness to light is graded on a scale from 1 to 8 as indicated in International Organization for Standards (ISO) 105 B02 wherein a lower number on the scale corresponds to a pigment that degrades more rapidly compared to a pigment with a higher number on the scale. The fastness to light of the pigment can vary depending on the estimated life of the plastic article that is being measured and the carrier material that is employed in the formulation. Stated another way, the pigment can be selected based on the fastness to light such that the pigment degrades at a rate faster than or equal to the degradation of the plastic article to be measured.

While the choice of pigment can vary depending on the application and carrier material, the pigment can be selected to follow the degradation of the plastic article, can follow a time interval that is predetermined by legislation or other regulation, and the like. For example, it is possible to realize color shifts from violet to white or red to transparent under the action of a suitable predetermined quantity of UV radiation. In one embodiment, a suitable pigment includes Color Index (C.I.) Pigment red 48:30.

In one embodiment, the indicator device comprises a homogeneous mixture of two or more different pigments, each having a different fastness to light such that the indicator device displays different colors as it is exposed to UV radiation. For example, it is possible to mix red and yellow pigment, wherein the yellow pigment is faster to light than the red pigment. Initially, the indicator device appears as red, but as the red pigment disappears, the indicator device changes to yellow. In due course, the yellow colored pigment also disappears and the indicator device changes to white. This color change gives the end user a forewarning that the service life of the article to which the indicator device corresponds is approaching its end. As a result, new objects can be ordered in good time, which is an advantage on planned purchasing and stock-keeping.

In another embodiment, the indicator device comprises multiple layers or sections, wherein each layer or section comprises a different pigment. For example, multiple layers are disposed in contact with each other, wherein each layer has a pigment with a different fastness to light than the respective pigment(s) employed in each other layer. As each layer is exposed to UV radiation, the pigment in each respective layer begins to degrade. Over time, the pigment in the outer most layer degrades completely exposing the pigment of the next layer, which provides a visual indication of the aging of the article. It is briefly noted that the multiple layers can be formed by any suitable method (e.g., injection molding, coextrusion, lamination, and the like).

As briefly mentioned, the indicator device can comprise multiple sections disposed adjacent to each other in the same planar direction. For example, in one embodiment, the indicator device comprises a disc-like shape, which is formed by joining multiple wedge-like shapes (sections) together to form the disc-like shape. Each section comprises a different pigment having a different fastness to light. Stated another way, the pigment of each section degrades at a different rate, which provides a visual indication of the aging of the article. For example, an indication that the useful life of the article has been depleted occurs when the color of all the sections are the same color.

The degradation of the pigment, and thereby the color of the indicator device, can also be affected by the material thickness of the carrier material of the indicator device. More particularly, pigment that lays most proximal to the surface of the indicator device is affected first and to the greatest extent when compared to the pigment laying deeper, which is affected only when the surface pigment has been broken down. Thus, the color tends to disappear first in the relatively thinnest part of the indicator device, while areas of greater material thickness can maintain the pristine color longer than the thinnest part.

Further, while the amount of pigment degradation can vary with the thickness of the indicator device, the pigment is present in an amount sufficient to allow the pigment to degrade at a time shorter than or equal to a time in which the plastic article degrades. For example, the formulation comprises about 0.5 wt. % to about 10 wt. % pigment, more particularly about 1 wt. % to about 5 wt. %, even more particularly 1 wt. % to about 3 wt. %, wherein the weight percents are based on a total weight of the formulation.

It is noted that by varying the material thickness of the indicator device, a multi-stage (e.g., stepwise) indication is obtained, which indicates the remaining life of the article. For example, each stage can represent a fraction of useful life of the article, such that a color change at each step indicates to the end user of the article that remaining fraction of useful life remaining or the fraction of life depleted.

In various embodiments, the formulation further comprises an UV stabilizer, which is compatible with the carrier material and the pigment. The UV stabilizer employed is selected to maintain the properties of the pigment (e.g., does not affect the manner in which the pigment degrades when exposed to UV light). Suitable UV stabilizers include hindered amine light stabilizers (Hals), UV absorbers, and the like. In one embodiment, the UV stabilizer is present in an amount up to about 1 wt. %, particularly about 0.2 wt. % to about 0.5 wt. %, wherein the weight percents are based on a total weight of the formulation.

The carrier material, the pigment, the optional UV stabilizer, and any other additive(s) can be mixed together by any suitable method to form the formulation employed in the indicator device. Suitable methods include blending (e.g., melt blending), mixing (e.g., admixing), and the like. For example, the components of the formulation can be disposed in a hopper and extruded into sheets, which can be employed in the indicator device. Suitable methods of forming the indicator device include, but are not limited to, extrusion (including coextrusion), molding, and the like, with molding being particularly beneficial in some applications where a relatively low cost indicator device is desired. Further, in various embodiments, an adhesive (e.g., a pressure sensitive adhesive (PSA) can be disposed on a surface of the indicator device by any suitable method (e.g., spraying, coating (e.g. cast coating), and the like).

The indicator device comprises any shape or size that is compatible with the plastic article. Further, the indicator device is affixed to the plastic article or disposed proximate to the plastic article. The indicator device can be affixed to the plastic article by any suitable fastening technique. For example, the indicator device can comprise an adhesive on a surface such that the surface comprising the adhesive can be fastened to a surface of the plastic article. In yet other embodiments, the indicator device can comprise a threaded portion corresponding to a threaded portion of the plastic article. Suitable other fasting techniques include, but are not limited to, snaps, buttons, and hook and loop fasteners. In some embodiments, the indicator is non-removably affixed to the plastic article to ensure that both the indicator and the article are exposed to the same conditions.

Without wanting to be bound by theory, the location of the indicator device is desirably positioned to receive maximum UV exposure. For example, the plastic article can be a hardhat (helmet) that is employed, for example, in the construction industry. In this example, the indicator device can be positioned on a brim of the hat, a side of the hat, a top portion of the hat, and the like.

Figure 2:
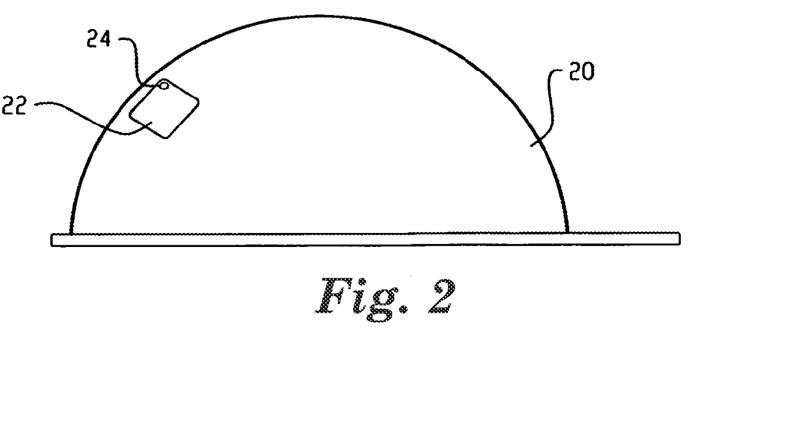
FIG. 2 is a side view of a helmet comprising an embodiment of an indicator device.

Referring now to FIG. 2, a helmet, generally designated 20, comprises an indicator device 22 non-removably affixed to a side of the helmet 20. The indicator device is secured to the helmet 22 by some form of securing component 24. Suitable fixing devices include, but are not limited to, rivet, screws, and adhesives (as discussed above). Other methods of securing the indicator device 22 to the helmet 20 include, but are not limited to, casting, laminating, gluing, and cementing. In one embodiment, the helmet and indicator device is non-removably affixed to comply with any safety regulations placed on the helmet by various governmental agencies.

Figure 3A:
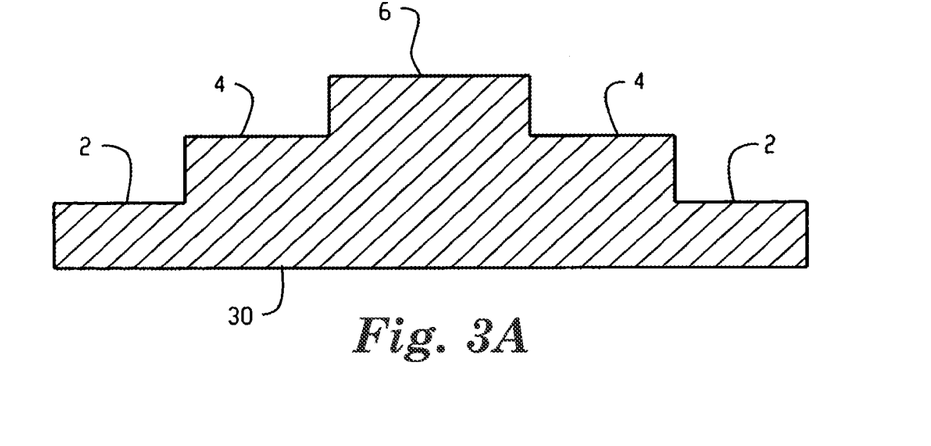
FIG. 3A is a cross sectional view of an embodiment of an indicator device.

Referring now to FIG. 3A, an embodiment of an indicator device, generally designated 30, is illustrated. The indicator device 30 comprises varying material thickness illustrated as discrete steps. More particularly, a first step 2 is relatively thinner to a second step 4, which in turn is relatively thinner than a third step 6. In this example, the color fades at the thinnest step 2 first followed sequentially by the second step 4 and the third step 6. The thickness of each step and the number of each step varies depending on the desired application.

Figure 3B:
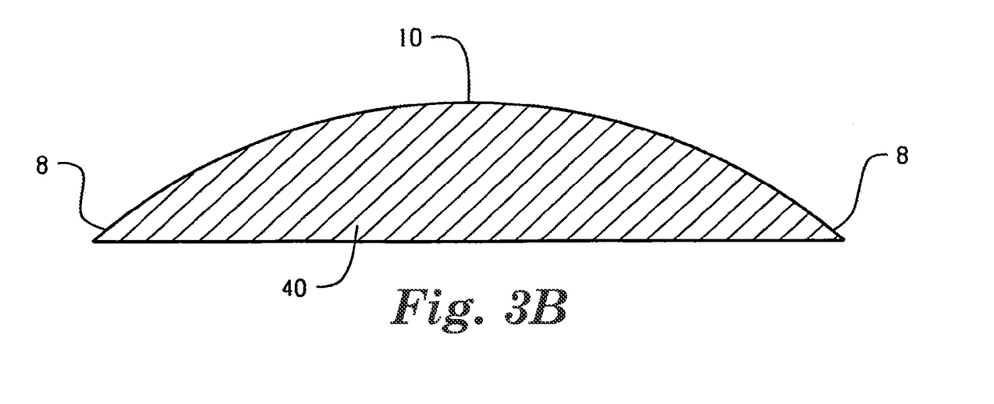
FIG. 3B is a cross sectional view of another embodiment of an indicator device.

In FIG. 3B, another embodiment of an indicator device, generally designated 40, is illustrated. The thickness of the indicator device 40 varies steplessly from an edge portion 8 to a central portion 10. For example, the edge portion 8 is the thinnest portion of the indicator device 40, with the central portion being the thickest portion of the indicator device 40. The gradual color change from the edge portion 8 to the central portion 10 provides a visual indication of the remaining life of the article as discussed above.

Figure 4:
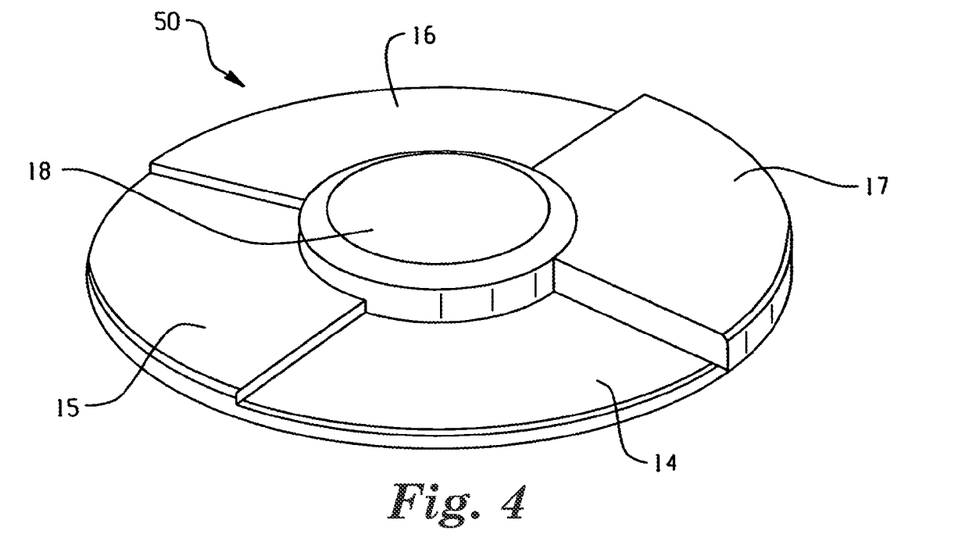
FIG. 4 is a perspective view of a third embodiment of an indicator device.
Figure 5:
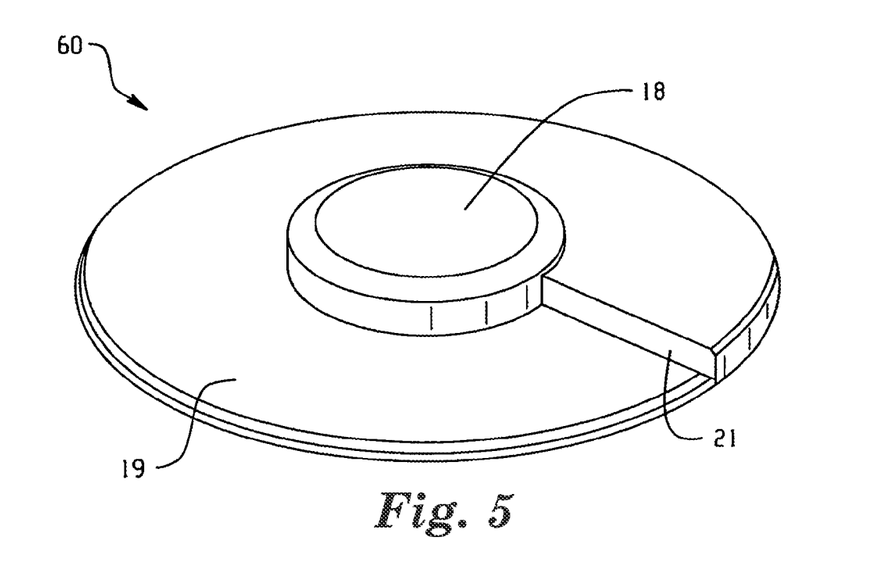
FIG. 5 is a perspective view of a fourth embodiment of an indicator device.

FIGS. 4-5 each respectively further illustrate an indicator comprising steps and an indicator that is stepless. More particularly, FIG. 4 illustrates an indicator device generally designated 50 comprising steps 14, 15, 16, and 17 and a central portion 18. The indicator device 50 is illustrated as comprising a disc-like shape, in which a thickness of each step increases in a clockwise direction when starting at step 14, with the central portion 18 comprising the thickest portion of the indicator device. As such, in this example, the central portion 18 is the last portion to change color. FIG. 5 illustrates another embodiment of an indictor device, generally designated 60. The indicator comprises a central portion 18 similar to that described in FIG. 4 and a surrounding zone 19 having a thickness that increases continuously in a clockwise direction until a complete circle has been passed and a discontinuity in the form of a step 21 occurs.

Figure 6A:
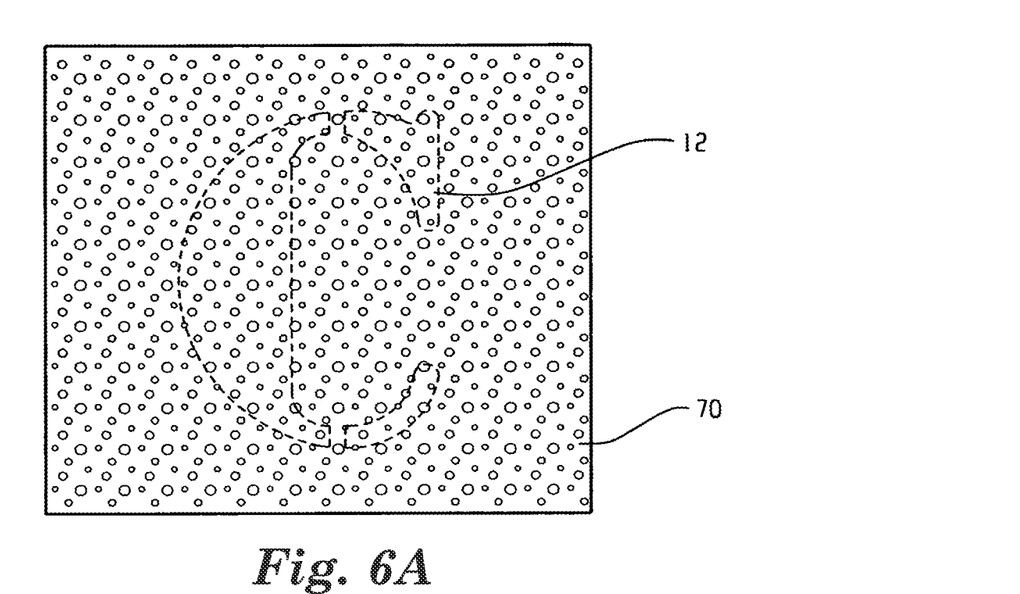
FIG. 6A is a plain view of a third embodiment of an indicator device in a pristine state.
Figure 6B:
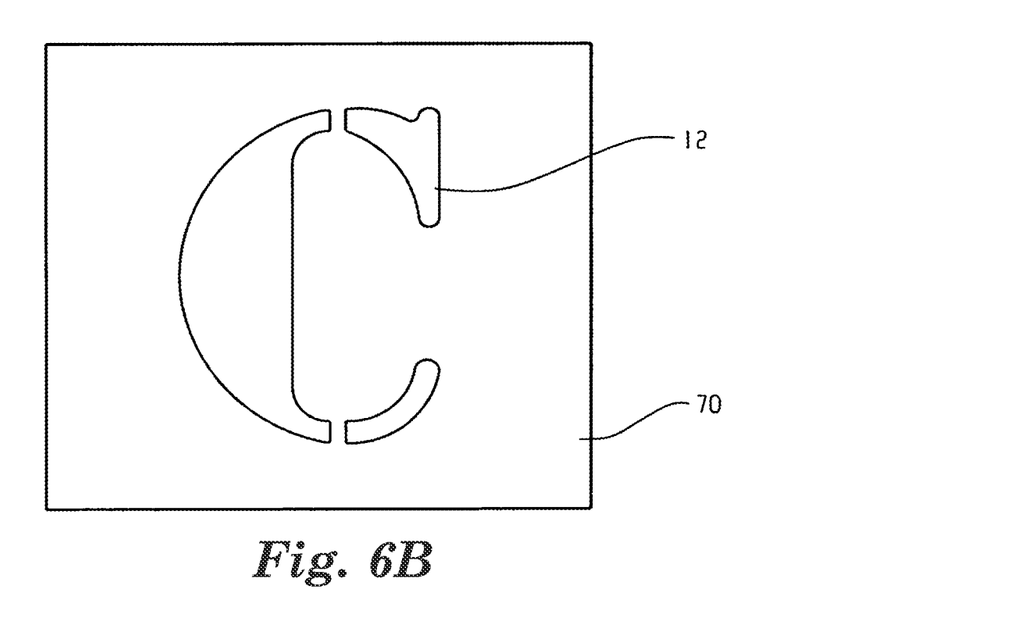
FIG. 6B is a plain view of the embodiment of FIG. 6A in an aged state.

In addition to the color change providing a visual indication of the remaining life of the article, a marking can be employed to provide a visual indication of the useful life of the article to the end user. For example, the marking can be a scale indicating the remaining useful life of the article. Additionally/alternatively, in other embodiments, the marking includes lettering, which forms words (e.g., "warning", "caution", "dispose", and the like), which is illustrated in FIGS. 6A and 6B as the letter "C". For example, in FIG. 6A, an indicator device, generally designated 70, is illustrated. The indicator device 70 comprises a marking 12, which is covered by a carrier material comprising a pigment, which is represented in FIG. 6A as a plurality of dots. In FIG. 6A, the indicator device 70 is in a pristine state, wherein the indicator devices has not been exposed to a sufficient quantity of UV radiation to allow the marking 12 (e.g., the letter C in each of FIGS. 6A and 6B) to be seen through the carrier material. Stated another way, the pigment conceals the marking 12. In contrast to FIG. 6A, the indicator device 70 as illustrated in FIG. 6B has aged by exposure to UV radiation to an extent that the marking 12 is completely visible, which further signals to the end user to replace the article.

In one embodiment, the marking 12 comprises a color substantially the same as the color of the pigment, such that the pigment easily conceals the marking 12 prior to UV exposure. As the pigment degrades, the marking 12 becomes visible. The pigment of the marking 12 is selected such that it degrades at a rate less than the pigment of the carrier material. The marking 12 is cast into the indicator device 70. In other embodiments, the marking is disposed (e.g., printed, glued, and the like) onto an underside (i.e., a side opposite a side facing the end user of the indicator device 70, which can be in physical communication with the article) of the indicator device 70. Further, it is to be understood that any combination of markings, pigments, layers, segments, and any other feature described in this disclosure can be employed depending on the desired application.

EXAMPLES

The following are exemplary formulations that were developed for use in the indicator devices discussed throughout this disclosure. Unless otherwise indicated, the weight percents included in the chart were based on the total weight of the formulation.

TABLE 1

|  | Sample 1 | Sample 2 | Sample 3 | Sample 4 | Sample 5 | Sample 6 | Sample 7 | Sample 8 |
|---|---|---|---|---|---|---|---|---|
| Polyethylene (Stamylan HD 7058Z) | 98.8 | 99.2 | 99.5 | 96.3 | 98.8 | 96.8 | 98.8 | 96.8 |
| Hals (Chimassorb 944)* | 0.2 | 0.2 | 0.2 | 0.2 | 0.2 | 0.2 | 0.2 | 0.2 |
| 30% Pigment red 48:3; Sr salt of a monoazo acid dye (MB 4111 Röd Polystatic) | 1.0 | 0.6 | 0.3 | 0.5 | 0 | 0 | 0 | 0 |
| Fluorescent pigment (12-2030-LMP5) | 0 | 0 | 0 | 3.0 | 1.0 | 3.0 | 1.0 | 3.0 |

*Chimassorb is a product designation of Ciba Specialty Chemicals.

The indicator devices disclosed herein are used to measure the life of any article that degrades upon exposure to UV radiation. Suitable articles include articles made of plastic. For example, plastic articles include, but are not limited to, helmets (e.g. bicycle helmets, construction helmets, and the like), car seats, bicycle seats, earmuffs, face shields, box carrier, chairs, and boat hulls. Non-plastic articles that employ the indicator device include, but are not limited to foods, clothes, and the like.

It is advantageously noted that the indicator device disclosed herein provides an indication of the lifetime of an article that degrades upon UV exposure. The visual indication provided by the indicator device allows the article to be replaced as needed, rather than for example by some arbitrary date marking. As such, new articles can be ordered in good time, which is an advantage on planned purchasing and stock-keeping. Further, as noted above, considerable economic losses can be suffered by manufactures, retailers, end-users, and the like, who might have stored large quantities of the dated marked articles, this indicator allows the same large quantity of articles to be stored with the benefit of an indication of the UV exposure of each article, thereby providing the indication of remaining useful life of the article.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method of measuring UV degradation of a plastic article,
    the method comprising the steps of:
    providing a plastic article;
    providing a UV indicator comprising a carrier material having a thickness and a pigment degradable by exposure to UV radiation, the pigment being disposed in the carrier material; and
    employing the UV indicator to provide a visible indication related to a useful life of the plastic article, the employing step comprising exposing the plastic article together with the UV indicator to substantially the same cumulative amounts of UV radiation for the useful life of the plastic article, wherein UV degradation of the pigment corresponds to UV degradation of the plastic article, and using UV degradation of the pigment to provide the visible indication related to a remaining useful life of the plastic article.

2. The method of claim 1, wherein the plastic article comprises a helmet.

3. The method of claim 1, wherein the visible indication comprises a color change.

4. The method of claim 1, wherein the carrier material has a varying thickness.

5. The method of claim 4, wherein the visible indication comprises color disappearing first in a thinner part of the carrier while areas of greater material thickness maintain color.

6. The method of claim 4, wherein the visible indication comprises a stepwise visible change from a thinner part of the carrier material to a thicker part of the carrier material connected by a stepwise transition.

7. The method of claim 4, wherein the visible indication comprises a plurality of stepwise visible changes, each from a thinner part of the carrier material to a thicker part of the carrier material connected by a stepwise transition, the change at each step indicating a remaining fraction of useful life of the plastic article remaining or a fraction of useful life of the plastic article depleted.

8. The method of claim 4, wherein the visible indication comprises a gradual visible change along a surface of the carrier material having a gradually increasing thickness.

9. The method of claim 1, wherein the visible indication relates to a maximum permitted UV exposure of the plastic article.

10. The method of claim 1, wherein the visible indication comprises exposing a marking initially concealed by the pigment upon degradation of the pigment.

11. The method of claim 1, further comprising the step of attaching the UV indicator to the plastic article.

12. A system for determining ageing of a plastic article, the
    system comprising:
    a plastic article;
    a UV indicator comprising a first carrier material having a varying thickness and a first pigment degradable by exposure to UV radiation, the first pigment being disposed in the first carrier material;
    wherein the UV indicator is configured to be affixed to the plastic article such that the indicator device and the plastic article would receive substantially the same cumulative amounts of UV radiation;
    wherein the first carrier material, the thickness of the first carrier material, and the first pigment are selected and configured such that, upon exposure to UV radiation, UV degradation of the first pigment corresponds to UV degradation of the plastic article, and UV degradation of the first pigment provides a visible indication related to a remaining useful life of the plastic article.

13. A system for determining ageing of a plastic article, the
    system comprising:
    a plastic article;
    a UV indicator comprising a first carrier material having a thickness and a first pigment degradable by exposure to UV radiation, the first pigment being disposed in the first carrier material;
    wherein the first carrier material, the thickness of the first carrier material, and the first pigment are selected and configured such that, upon exposure to UV radiation, UV degradation of the first pigment corresponds to UV degradation of the plastic article, and UV degradation of the first pigment provides a visible indication related to a remaining useful life of the article; and
    wherein the first carrier material comprises a material having a useful life greater than or equal to the useful life of the plastic article.

14. The system of claim 12, wherein the UV indicator further comprises a second pigment disposed in the first carrier material, the first pigment having a different fastness to light than the second pigment, wherein the first carrier material, the thickness of the first carrier material, and the first and second pigments are selected and configured such that, upon exposure to UV radiation, UV degradation of the first and second pigments provide a visible indication related to a useful life of the article.

15. The system of claim 14, wherein the carrier material comprises a first layer and a second layer, the first layer comprising the first pigment and the second layer comprising the second pigment.

16. The UV indicator as recited in claim 12, further comprising a second carrier material having a thickness and a second pigment disposed in the second carrier material, the second pigment capable of degradation by exposure to UV radiation, and the second pigment having a different fastness to light than the first pigment, wherein the second carrier material, the thickness of the second carrier material, and the second pigment are selected and configured such that, upon exposure to UV radiation, UV degradation of the second pigment provides a visible indication related to a useful life of the article.

17. The UV indicator as recited in claim 12, further comprising a marking concealed by the first pigment, the marking capable of being revealed upon degradation of the first pigment to provide the visible indication.

* * * * *

UNITED STATES PATENT AND TRADEMARK OFFICE
CERTIFICATE OF CORRECTION

PATENT NO. : 9,615,619 B2  
APPLICATION NO. : 13/027571  
DATED : April 11, 2017  
INVENTOR(S) : Jan Folkesson It is certified that error appears in the above-identified patent and that said Letters Patent is hereby corrected as shown below:

In the Specification

Column 1
Line 8, delete "Aug. 11, 2004," and insert -- Oct. 25, 2005, --, therefor.

Column 2
Line 2, delete "manufactures," and insert -- manufacturers, --, therefor.

Signed and Sealed this  
Eleventh Day of July, 2017

Joseph Matal  
*Performing the Functions and Duties of the*  
*Under Secretary of Commerce for Intellectual Property and*  
*Director of the United States Patent and Trademark Office*